United States Patent
Beck et al.

(10) Patent No.: US 7,241,911 B2
(45) Date of Patent: Jul. 10, 2007

(54) NIOBIUM COMPOUND

(75) Inventors: Karsten Beck, Goslar (DE); Hady Seyeda, Goslar (DE); Udo Sulkowski, Vienenburg (DE); Axel Rosenkranz, Bad Harzburg (DE)

(73) Assignee: H. C. Starck GmbH & Co. KG, Goslar (DE)

( * ) Notice: Subject to any disclaimer, the term of this patent is extended or adjusted under 35 U.S.C. 154(b) by 0 days.

(21) Appl. No.: 11/238,362

(22) Filed: Sep. 29, 2005

(65) Prior Publication Data

US 2007/0073072 A1   Mar. 29, 2007

(51) Int. Cl.
*C07F 9/00*   (2006.01)
*C01G 33/00*   (2006.01)
(52) U.S. Cl. ............... 556/42; 423/67; 423/594.17; 423/594.8
(58) Field of Classification Search ........... 556/42; 423/594.17, 594.8, 67
See application file for complete search history.

(56) References Cited

OTHER PUBLICATIONS

Eriksson et al., Crystal Structure of Ammonium Diaquadioxalatooxoniobate(V) Dihydrate, NH4[NbO(C2O4)2(H2O)2]•(H2O)2, Acta Chemica Scandinavica, vol. 47, pp. 1038-1040 (1993).*

Brničević et al., Journal of the Less-Common Metals, vol. 45, pp. 45-52 (1976).*

Chemical Reviews, 99, (month unavailable) 1999, pp. 3603-3624, Izabela Nowak et al, "Niobium Compounds: Preparation, Characterization, and Application in Heterogeneous Catalysis".

Russian Journal of Inorganic Chemistry, vol. 9, No. 10, Oct. 1964, pp. 1288-1291, T.F. Limar et al, "Oxalato-Compounds of Niobium".

* cited by examiner

*Primary Examiner*—Porfirio Nazario-Gonzalez
(74) *Attorney, Agent, or Firm*—Connolly Bove Lodge & Hutz LLP

(57) ABSTRACT

The present invention relates to novel, water-soluble niobium compounds, a process for their preparation and their formulations.

14 Claims, 1 Drawing Sheet

NIOBIUM COMPOUND

Figure 1:
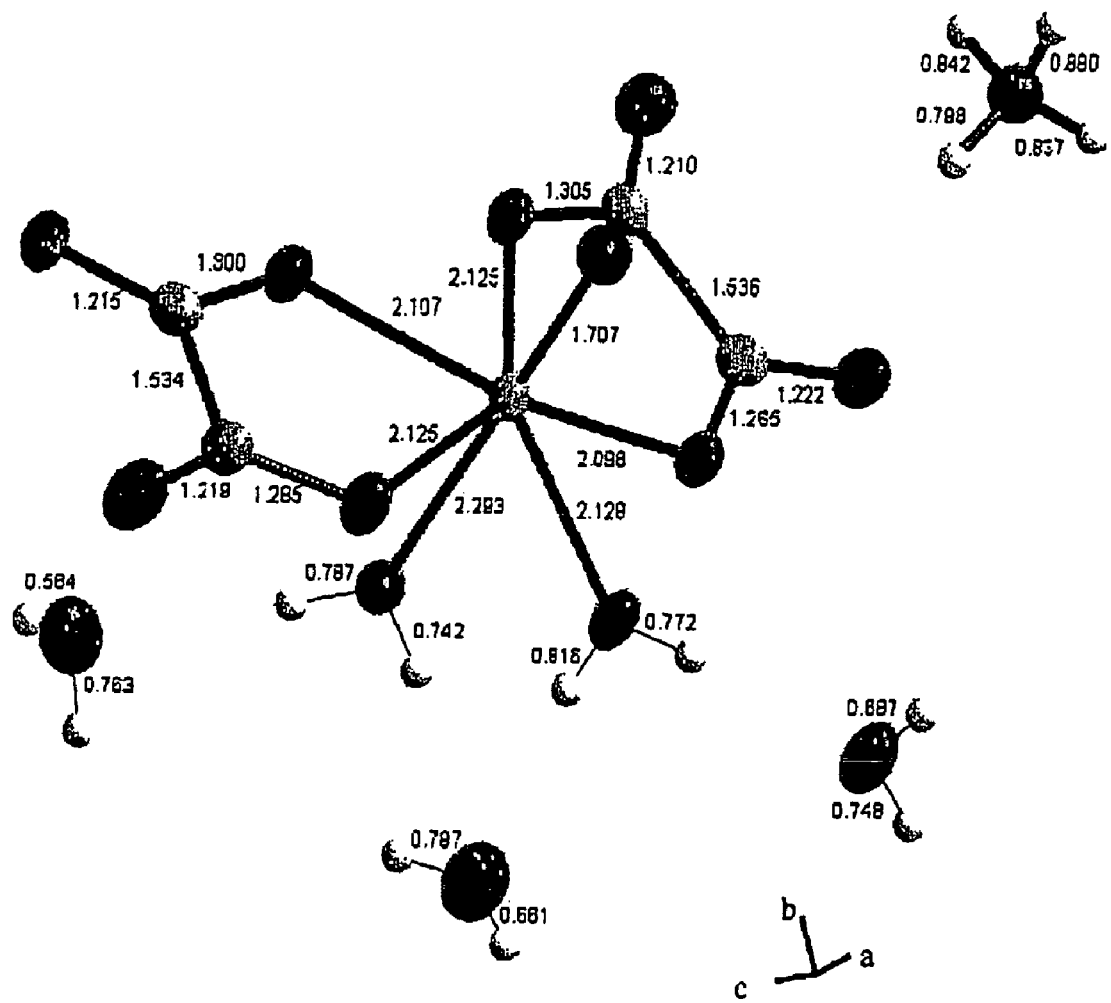

The present invention relates to a novel niobium compound, a process for its preparation and formulations comprising said niobium compound.

Niobium compounds are, amongst other applications, suitable to be used as dopants for certain catalysts or ferrites.

In this application, the catalyst carrier or active species will be mixed with the dopant and calcined in a subsequent process step. The calcination usually takes place under conditions where the niobium compound is converted to pure niobium pentoxide. Such applications encompass, but are not limited to, ethane hydrogenolysis, dehydrogenation of hydrocarbons, solid acid catalysis in polycondensation, or ammoxidation. Such catalysts in which niobium compounds are used are in particular catalysts to convert butane to acrylonitrile in the presence of ammonia and oxygen, conversion of butane to acrolein in the presence of oxygen (oxidation), oxidative dehydrogenation of alkanes, like conversion of propane to propene. Such applications are, for example, disclosed in Chemical Reviews 1999, (99), 3603–3624, which is enclosed by reference for all useful purposes. Mixing with the niobium compound often takes place in an aqueous solution, suspension or emulsion.

For such applications it is important that the niobium compound exhibits excellent water solubility, yields pure niobium pentoxide with no impurities from complexing agents or counterions when calcined under appropriate conditions and has a high content of niobium in weight percent, so with addition of small amounts of the niobium compound an aqueous solution having a suitable high niobium concentration can be prepared.

Limar et al. in Russian Journal of Inorganic Chemistry, Vol. 9 No. 10, October 1964, pages 1288–1291, disclose the niobium oxalate complexes $Na[Nb(O)(C_2O_4)_2(H_2O)]*4 H_2O$ as well $(NH_4)_3[Nb(O)(C_2O_4)_3]*xH_2O$. These complexes, however, do not fully satisfy the conditions as set out above. With sodium as counteraction, sodium impurities will remain in the niobium pentoxide after calcination. The ammonium complex is 3-fold negatively charged resulting in lower niobium content. Coordination with three oxalate ions has the same effect of lowering the niobium content in percent by weight. Additionally, the water solubility of merely 20 g Nb/l and 40 g Nb/l, respectively, needs to be significantly improved.

It was an object of the invention to provide a niobium compound exhibiting excellent water solubility (greater than 30 g Nb/l), which yields niobium pentoxide with a purity of at least 99%, consequently comprising up to 1% impurities fom complexing agents or counterions when calcined under appropriate conditions, and has a high content of niobium (greater than 22 percent by weight) in weight percent. This problem is solved by the niobium compound ammonium (bisaquo oxobisoxalato)niobate $(NH_4)[Nb(O)(C_2O_4)_2(H_2O)_2]$, and the corresponding trihydrate, ammonium-(bisaquo oxobisoxalato)niobate-trihydrate $(NH_4)[Nb(O)(C_2O_4)_2(H_2O)_2]*3 H_2O$, of formula 1.

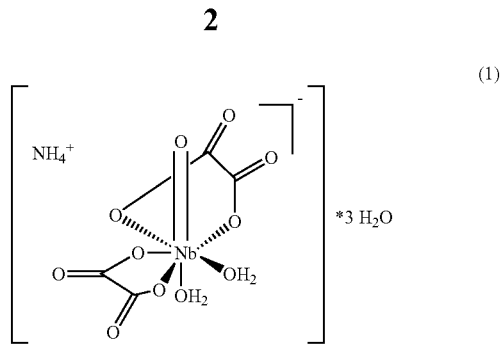

(1)

The compound according to the invention yields niobium pentoxide with a purity of 99% and not more than 1% of impurities from complexing agents or counterions when calcined under appropriate conditions. Preferably, the compound has a purity of at least 99.9%, in particular at least 99.99%. FIG. 1 shows the three-dimensional structure of the compound according to the invention as determined by X-ray structure analysis. The numbers show the respective bond lengths in Angström.

The compound according to the invention exhibits excellent water solubility of 52 g Nb/l (grams niobium per litre) at 20° C. and a maximum solubility of 114.8 g Nb/l at a temperature of 50° C. in comparison to the prior art compounds with solubilities as set out above.

The compound according to the invention has a niobium content of 24.3 weight percent, while the prior art compound $(NH_4)_3[Nb(O)(C_2O_4)_3]$ has a niobium content of merely 21.8 weight percent of niobium. The high percentage of niobium in the material is economically advantageous because all other elements in the complex like nitrogen and carbon will be removed during calcination.

Other counterions than ammonium are usually unsuitable, since other counterions such as alkaline ions will either cause impurities on calcination while ammonium does evaporate as gaseous ammonia, or such cations have a higher molecular weight than ammonium ions thus causing a lower weight percentage of niobium.

The present invention also relates to a process for making the compound according to the invention.

Prior art compounds were made by dissolving niobium hydroxide and ammonium oxalate in water and, in a subsequent step, either reducing the volume by subsequent reduction of water or addition of acetone in order to reduce the solubility of the niobium compound, which in both cases does precipitate. The niobium concentration is about 2 mol Nb/l (mole niobium per liter).

In contrast thereto, in the process according to the present invention niobium hydroxide and oxalic acid are dissolved in water and gaseous ammonia is passed through. The ammonia dissolves and neutralizes the oxalic acid, which causes warming to about 35° C. to about 50° C., preferably about 40° C. to about 45° C. In order to speed up the reaction it is also possible to heat up the reaction mixture to not more than 80° C., preferably less than 70° C., and more specifically about 60° C.

The sequence of the addition is preferably niobium hydroxide, oxalic acid and ammonia. The educts are usually added into water during agitation. The addition of the educts may be carried out at once, although addition in portions is preferred, in particular if larger amounts of the compound according to the invention are to be produced.

The molar ratio of niobium to oxalic acid is 1:2.8, whereas the calculation is based on the molecular weight of oxalic acid including crystal water.

The concentration of Niobium must be less than about 2 mol Nb/l, preferably from about 1.4 mol Nb/l to about 1.9 mol Nb/l, in particular from about 1.5 mol Nb/l to about 1.7 mol Nb/l, more specifically about 1.6 mol Nb/l or less.

An aqueous ammonia solution may be used instead of gaseous ammonia, provided the niobium concentration is at a suitable level as set out above.

Preferably, an aqueous solution comprising 25% by weight of ammonia is used for the process according to the invention.

The pH-value of the reaction mixture is less than about 3.5, more specifically the pH-value of the reaction mixture is from about 1 to about 3, particularly from about 1 to about 2.

The amount of the ammonia added is suitable to achieve this pH value and can easily calculated by the artisan.

After the addition of ammonia has finished, the reaction mixture is allowed to cool to a temperature of about 25° C. or less, in particular to from 10° C. to 23° C., or from 15° C. to 22° C., or from 18° C. to 20° C.

Depending on the amount of reaction mixture active cooling is required to achieve cooling in a reasonable time, that is, cooling to the desired temperature in 24 hours or less. The active cooling may be carried out by any suitable means known to the artisan, like external cooling of the reaction container or by means of circulation of a coolant through a heat exchanger which is placed inside the reaction container.

Preferably, the cooling from 40° C. to 20° C. takes place within 4 hours. The average cooling rate throughout the cooling time is in the range of from about 3° C./hour to about 10° C./hour, preferably from about 4° C./hour to about 8° C./hour, in particular about 5° C./hour.

The reaction product does precipitate during cooling, is filtered off from the reaction mixture and subsequently dried at a temperature of less than about 80° C., preferably less than about 75° C., in particular at about 70° C. Drying may take place in air, in an inert gas such as argon or nitrogen or under reduced pressure, in the presence of either air or an inert gas.

Further purification may be achieved by additional recrystallization. Preferably, said recrystallization is carried out using water as solvent. The drying step as set out above can be carried out in the same way to achieve removal of the water.

It was surprisingly found that a reaction product with higher niobium content was prepared, although the niobium concentration in the reaction mixture is lower than in the processes according to the prior art. For this reason, the process according to the present invention is also more economical as less energy is consumed, no organic solvents are involved and a higher niobium content of the resulting compound can be achieved.

The present invention also relates to formulations comprising the compounds according to the present invention, ammonium(bisaquo oxobisoxalato)niobate $(NH_4)[Nb(O)(C_2O_4)_2(H_2O)_2]$.

In the most simple case the formulation according to the invention comprises ammonium(bisaquo oxobisoxalato)niobate $(NH_4)[Nb(O)(C_2O_4)_2(H_2O)_2]$ and water. Such a formulation may be a saturated aqueous solution of the compound in water or may be an aqueous slurry, but may contain additional ingredients such as adjuvants, like emulators or antimicrobia, like fungicides, herbicides or bactericides. Preferably, the formulation comprises oxalic acid and/or ammonium oxalate. More preferably, the oxalic acid and/or ammonium oxalate is present in an amount of between. 5% by weight to 10% by weight, more preferably between 7% by weight and 9% by weight, more specifically 8% by weight. The weight percentages describe the amount of oxalic acid and ammonium oxalate each.

The compound may be irritating to the skin or respiratory organs of humans or might affect the health and well-being of humans or have disadvantageous effects to plants, animals or the environment. For these reasons it is preferred if the compound according to the invention is provided in a form less prone to raise dust and thus exposing the surrounding with the compound in an uncontrolled manner. Additionally, providing the compound according to the invention in a defined amount provides for easy gravimetric or volumetric metering.

Such solutions or slurries are suitable for volumetric metering.

For gravimetric metering, which is used even more often and for which exposition and dusting is not only to be avoided during actual metering the material, but also during weighing, it is preferred to put a defined amount of the compound according to the invention into a container which is being destroyed when used, e.g. a bag.

More specifically, the formulation according to the invention also includes a defined amount of the compound according to the invention being inside a bag. Preferably, this bag is soluble in the reaction medium the niobium compound according to the invention is used for producing catalysts or ferrites. Most preferably, the bag is a water soluble polymer, like the bags described in international Patent Applications WO 9845185, WO 9737903 and US patent U.S. Pat. No. 5,666,785, as well as "Verpackungs-Rundschau", November 1997, page 40, which are incorporated by reference for all useful purposes.

It is particularly preferred that, although the bag dissolves when put into water, the inner side is equipped to be water resistant. In this way, an aqueous solution or slurry can be put into a water soluble bag and put into an aqueous reaction medium. The present invention thus also relates to a formulation comprising a container made of a soluble polymeric film comprising the compound according to the invention, its solution or its slurry. In a preferred embodiment, the polymeric film is a film comprising polyvinyl alcohol. In another preferred embodiment, the formulation is a slurry or a powder of the niobium compound according to the invention inside a closed bag comprising a film of polyvinyl alcohol.

In another embodiment, the formulation is a solid niobium compound according to the invention inside a closed bag comprising a film of polyvinyl alcohol.

Because the process according to the present invention is more economical, less energy consuming, no organic solvents are involved and a higher niobium content of the resulting compound can be achieved, the present invention also is a contribution to the protection of the environment.

The invention thus also relates to a process for protecting the environment comprising the preparation of niobium compounds by a process consuming a reduced amount of energy, not involving organic solvents. In a preferred embodiment, this process does as well provide compounds having increased niobium content.

The invention also relates to a method for creating a product specification for a batch, lot, or shipment of a chemical material, preferably a compound according to the invention, comprising specifying at least one property value for said batch, lot, or shipment. The property value may be a property value either specific for the chemical compound, like chemical formula, molecular weight, weight percentage of a certain element, melting point, boiling point or the like, or a property value specific to the lot, batch or shipment, like purity, a batch number or lot number, a list of ingredients of the formulation, grain size, shape of the particles, particle size distribution or the like.

In particular, such method comprises the step of specifying at least one property value per lot, batch or shipment, archiving the property values of said lots, batches or shipments in connection with information identifying the lot, batch or shipment, selecting at least one property value of at least one lot, batch or shipment, putting together the product specification by arranging the at least one property value of the identified said lot, batch or shipment in connection with information identifying the lot, batch or shipment and creating the product specification by displaying the at least one property value together with information identifying the lot, batch or shipment.

Displaying within the meaning of this invention may be creating a paper copy of the product specification by, for example, printing by a computer printout or conventional printing, but also involves displaying the product specification on a computer screen.

The display can be effected by a computer program having access to the archive of at least one property value in connection with information identifying the lot, batch or shipment, or by means of an internet webpage displayed in a web browser.

In a further embodiment, the method for creating a product specification is a method wherein the property value is included on a product specification sheet, purchase order, invoice, contract, waiver to a contract, or combinations thereof for the batch, lot, or shipment of a compound. Preferably, the compound is a compound according to the invention, or a different niobium compound, in particular a niobium oxalate complex.

In yet another embodiment of the invention the method for creating a product specification, is a method wherein said specifying comprises determining at least one property value for said batch, lot, or shipment of particulate material. Determining comprises measuring or analyzing said batch, lot, or shipment by conventional measuring methods and thus determining either a property value specific for the lot, batch or shipment, or being specific for the chemical compound. If the property value to be determined is a property value specific to the chemical compound, the determining step does also encompass accessing the property value specific to the chemical compound in a directory comprising such property values. The directory may be available in physical form in a library or in the form of an electronic database. In the latter case, said determining can be carried out by means of a computer program.

In a further embodiment of the invention, the method for creating a product specification is a method wherein said specifying comprises characterizing the batch, lot, or shipment of particulate material by at least one interfacial potential value.

In a further embodiment, the method for creating a product specification further comprises the step of specifying at least one morphological value like surface area, particle size, structure, porosity, or combinations thereof, to said batch, lot, or shipment of particulate material.

The present invention also relates to a method of doing business with a customer comprising using a product specification that includes a property value to request a certain batch, lot, or shipment and/or to provide a certain batch, lot, or shipment of chemical material.

Such a process involves the steps of providing a product specification, preferably a product specification as set out above, to the customer, the customer choosing at least one property value of at least one lot, batch or shipment suitable for his purposes, identifying the lot, batch or shipment providing a chemical material suitable for the customers purposes, selecting said lot, batch or shipment and placing an order for said selected lot, batch or shipment.

Additionally, the method may further comprise the step providing the ordered lot, batch or shipment to said customer having selected the lot, batch or shipment.

The present invention also extends to a method for improving identification of a grade, type, or brand of chemical material comprising the step of updating an existing product description for the grade, type, or brand of particulate material by adding at least one property value.

The present invention also extends to a method for creating a product specification, a method for improving identification of a grade, type, or brand of chemical material as set out above or a method of doing business with a customer comprising using a product specification, wherein said product description is in a catalogue, web site, brochure, chemical material literature, advertisement, label, or combinations thereof.

EXAMPLES

Example 1

Niobium hydroxide (241 kg, niobium content: 23.6%*) was added to 30 L of water under stirring. Oxalic acid (225 kg) and aqueous ammonia (33 l, 25% by weight $NH_3$) were added subsequently. Addition of ammonia caused the solution to heat up to 40° C. The solution was stirred overnight and then cooled to 23° C., causing the desired niobium oxalate complex to precipitate out of the solution. The precipitate was filtered off and dried for about 20 h at 70° C., yielding 213 kg of the crude ammonium niobium axalate complex. Recrystallization from water yielded the pure $[NH_4][Nb(O)(C_2O_4)_2(H_2O)_2]*3H_2O$ complex.

Example 2

Niobium hydroxide (254 kg, niobium content: 24.7%*) was added to 34 L of water under stirring. Oxalic acid (238.4 kg) and aqueous ammonia (37 l, 25% by weight $NH_3$) were added subsequently. After addition of ammonia the solution was heated up to 61° C. and stirred for 9 hours at this temperature. Afterwards the solution was cooled to 24° C., causing the desired niobium oxalate complex to precipitate out of the solution. The precipitate was filtered off and dried for about 24 h at 78° C., yielding 204 kg of the crude ammonium niobium oxalate complex. Recrystallization from water yielded the pure $[NH_4][Nb(O)(C_2O_4)_2(H_2O)_2]*3H_2O$ complex.

* The niobium content of the niobium hydroxide is dependent on the water content of the batch used.

The invention claimed is:

1. A process for the preparation of a niobium compound, comprising the steps of:
   dissolving niobium hydroxide and oxalic acid in water;
   adding ammonia
   cooling the reaction mixture.

2. The process according to claim 1, wherein the niobium compound is $(NH_4)Nb(O)(C_2O_4)_2(H_2O)_2$ and hydrates thereof.

3. Process according to claim 1, wherein the niobium concentration in the reaction mixture is less than about 2 g Nb/l.

4. Process according to claim 1 or 2, wherein the reaction mixture has temperature of about 35° C. to about 80° C.

5. Process according to claim 1, wherein the reaction mixture is cooled to a temperature of about 25° C. or less.

6. Process according to claim 1, wherein the addition of ammonia is carried out by addition of aqueous ammonia or passing gaseous ammonia though the reaction mixture.

7. Process according to claim 1, wherein the process further comprises a filtration step.

8. Process according to claim 6, wherein the process further comprises a drying step.

9. Process according to claim 7, wherein the drying step is carried out at a temperature of less than about 80° C.

10. A formulation comprising a defined amount of $(NH_4)[Nb(O)(C_2O_4)_2(H_2O)_2]$ compound in a bag.

11. A formulation according to claim 9, wherein the bag is a bag soluble in water or a reaction medium.

12. A formulation comprising a container made of a soluble polymeric film comprising the compound $(NH_4)[Nb(O)(C_2O_4)_2(H_2O)_2]$, its solution or its slurry.

13. A formulation according to claim 11, the polymeric film comprising polyvinyl alcohol.

14. A formulation according to claim 11, said formulation being a solid $(NH_4)[Nb(O)(C_2O_4)_2(H_2O)_2]$ compound inside a closed bag comprising a film of polyvinyl alcohol.

* * * * *

UNITED STATES PATENT AND TRADEMARK OFFICE
CERTIFICATE OF CORRECTION

| | |
|---|---|
| PATENT NO. | : 7,241,911 B2 |
| APPLICATION NO. | : 11/238362 |
| DATED | : July 10, 2007 |
| INVENTOR(S) | : Karsten Beck et al. |

Page 1 of 2

It is certified that error appears in the above-identified patent and that said Letters Patent is hereby corrected as shown below:

On the Title Page:

In Notice: "under 35 U.S.C. 154(b) by 0 days" should read -- under 35 U.S.C. 154(b) by 4 days --.

In the Claims:

In Claim 4, in column 7, line 7 "Process according to claim 1 or 2" should read -- Process according to claim 1 or 3 --.

In Claim 8, in column 7, line 16 "Process according to claim 6" should read -- Process according to claim 7 --.

In Claim 9, in column 8, Line 1 "Process according to claim 7" should read -- Process according to claim 8 --.

In Claim 11, in column 8, line 5 "A formulation according to claim 9" should read -- A formulation according to claim 10 --.

In Claim 13, in column 8, line 10 "A formulation according to claim 11" should read -- A formulation according to claim 12 --.

UNITED STATES PATENT AND TRADEMARK OFFICE
CERTIFICATE OF CORRECTION

PATENT NO. : 7,241,911 B2
APPLICATION NO. : 11/238362
DATED : July 10, 2007
INVENTOR(S) : Karsten Beck et al.

It is certified that error appears in the above-identified patent and that said Letters Patent is hereby corrected as shown below:

In the Claims (cont'd):

In Claim 14, in column 8, line 12 "A formulation according to claim 11" should read -- A formulation according to claim 12 --.

Signed and Sealed this

Eighteenth Day of December, 2007

JON W. DUDAS
*Director of the United States Patent and Trademark Office*